United States Patent
Neukirchen et al.

(10) Patent No.: US 9,642,964 B2
(45) Date of Patent: May 9, 2017

(54) PERIODIC CONTRAST INJECTIONS AND ANALYSIS OF HARMONICS FOR INTERVENTIONAL X-RAY PERFUSION IMAGING

(71) Applicant: KONINKLIJKE PHILIPS N.V., Eindhoven (NL)

(72) Inventors: Christoph Neukirchen, Aachen (DE); Daniel Simon Anna Ruijters, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 276 days.

(21) Appl. No.: 14/380,176

(22) PCT Filed: Feb. 27, 2013

(86) PCT No.: PCT/IB2013/051568
§ 371 (c)(1),
(2) Date: Aug. 21, 2014

(87) PCT Pub. No.: WO2013/132390
PCT Pub. Date: Sep. 12, 2013

(65) Prior Publication Data
US 2015/0025370 A1    Jan. 22, 2015

Related U.S. Application Data

(60) Provisional application No. 61/607,044, filed on Mar. 6, 2012.

(51) Int. Cl.
A61B 5/05    (2006.01)
A61M 5/00    (2006.01)
(Continued)

(52) U.S. Cl.
CPC .............. *A61M 5/007* (2013.01); *A61B 6/025* (2013.01); *A61B 6/032* (2013.01); *A61B 6/4441* (2013.01);
(Continued)

(58) Field of Classification Search
CPC ........ A61M 5/007; A61M 5/32; A61M 5/315; A61B 6/4441; A61B 6/481; A61B 6/504; A61B 6/503; A61B 6/501; A61B 6/025
(Continued)

(56) References Cited

U.S. PATENT DOCUMENTS 6,236,706 B1 *   5/2001   Hsieh .................... A61B 6/032
                                                                    378/15
6,373,920 B1 *   4/2002   Hsieh .................... A61B 6/507
                                                                    378/8
7,925,330 B2 *   4/2011   Kalafut ............. A61M 5/14546
                                                                    600/431

OTHER PUBLICATIONS

Max Wintermark et al, "Dynamic Perfusion CT: Optimizing the Temporal Resolution and Contrast Colume for Calculation of Perfusion CT Parameters in Stroke Patients", AJNR, American Journal of Neuroradiology, vol. 25, No. 5, May 1, 2004, pp. 720-729.
(Continued)

*Primary Examiner* — Sanjay Cattungal (57) ABSTRACT

An apparatus (130) and a method for adjusting, in perfusion imaging system, a periodic contrast agent injection rate signal (IS) for an injector (135) as function of an image sampling rate determined by the rotational speed of an X-ray source (107)-detector (109) assembly of an X-ray imager (100). Frequency, periodicity and pulse width of the contrast agent injection rate signal (IS) is adjusted to mitigate temporal signal aliasing in a sample of a time attenuation contrast (TAC) signal.

17 Claims, 6 Drawing Sheets

(51) Int. Cl.

| | | |
|---|---|---|
| *A61B 6/03* | (2006.01) | |
| *A61B 6/00* | (2006.01) | |
| *A61B 6/02* | (2006.01) | |
| *A61K 49/04* | (2006.01) | |
| *A61M 5/172* | (2006.01) | |
| *A61M 5/315* | (2006.01) | |
| *A61M 5/32* | (2006.01) | |

(52) U.S. Cl.
CPC ............. *A61B 6/481* (2013.01); *A61B 6/486* (2013.01); *A61B 6/501* (2013.01); *A61B 6/503* (2013.01); *A61B 6/504* (2013.01); *A61B 6/507* (2013.01); *A61B 6/5217* (2013.01); *A61B 6/542* (2013.01); *A61K 49/04* (2013.01); *A61M 5/172* (2013.01); *A61M 5/315* (2013.01); *A61M 5/32* (2013.01); *A61M 2205/33* (2013.01)

(58) Field of Classification Search
USPC ................................................ 600/407–430
See application file for complete search history.

(56) References Cited

OTHER PUBLICATIONS

A. Fieselmann et al, "A Dynamic Reconstruction Approach for Cerebral Blood Flow Quantification with an Interventional C-Arm CT", Biomedical Imaging: From Nano to Macro, 2010, IEEE International Symposium on, IEEE, Piscataway, NJ, Apr. 14, 2010, pp. 53-56.

Kyongtae T. Bae et al, "Multiphasic Injection Method for Uniform Prolonged Vascular Enhancement at CT Angiography: Pharmacokinetic Analysis and Experimental Porcine Model", Radiology, Radiological Society of North America, Oak Broook, IL, vol. 216, No. 3, Sep. 1, 2000, pp. 872-880.

S. Kim et al, "Multiphasic contrast injection for improved precision of parameter estimates in functional CT", Medical Physics, AIP, Melville, NY, vol. 35, No. 12, Nov. 24, 2008, pp. 5921-5933.

P. Montes et al, "Dynamic Cone-beam Reconstruction for Perfusion Computed Tomography" PhD thesis, Univ. Heidelberg, (2006).

Christoph Neukirchen et al, "An iterative method for tomographic perfusion estimation in a decomposition model-based approach", Med. Phys. 37, (12) Dec. 2010, pp. 6125-6141.

Christoph Neukirchen, "An extended temporal interpolation approach for dynamic object reconstruction", 11th International Meeting on Fully Three-Dimensional Image Reconstruction in Radiology and Nuclear Medicine, pp. 379-382.

A. Ganguly et al, Cerebral CT Perfusion Usingan Interventional C-Arm Imaging System: Cerebral Blood Flow Measurements, American Journal of Neuroradiology, (2011), 32(8), pp. 1525-1531.

\* cited by examiner

PERIODIC CONTRAST INJECTIONS AND ANALYSIS OF HARMONICS FOR INTERVENTIONAL X-RAY PERFUSION IMAGING

CROSS-REFERENCE TO PRIOR APPLICATIONS

This application is the U.S. National Phase application under 35 U.S.C. §371 of International Application Serial No. PCT/IB2013/051568, filed on Feb. 27, 2013, which claims the benefit of U.S. Application Ser. No. 61/607,044 filed on Mar. 6, 2012. These applications are hereby incorporated by reference herein.

FIELD OF THE INVENTION

The present invention relates to an apparatus for supporting perfusion imaging, to a method for supporting perfusion imaging, to a medical x-ray for perfusion imaging, to a computer program element, and to a computer readable medium.

BACKGROUND OF THE INVENTION

Perfusion imaging may be used to gain clues on blood perfusion in soft tissue.

Currently, perfusion imaging is used mainly for purely diagnostic purposes where the imaging is achieved by a fast rotating CT system mounted in a closed gantry. Tomographic reconstruction methods are repeatedly applied to projections acquired in a series of fast rotations of the CT scanner's imaging module.

Knowledge on blood perfusion may also be useful in an interventional setting rather than a purely diagnostic, for example in planning support for neurological interventions.

A method for imaging blood perfusion is described in WO 2009/040742 where perfusion is mapped globally across large areas.

However, tomographic dynamic perfusion imaging methods for slowly rotating interventional imaging systems (for example of the C-arm type) where spatial resolution is substantially preserved are currently not available.

SUMMARY OF THE INVENTION

There may therefore be a need for a different perfusion imaging system.

The object of the present invention is solved by the subject matter of the independent claims wherein further embodiments are incorporated in the dependent claims.

It should be noted that the following described aspects of the invention equally apply to the method of supporting perfusion imaging, to the medical x-ray imaging for supporting perfusion imaging, to the computer program element and to the computer readable medium.

According to one aspect of the present invention there is provided an apparatus for supporting perfusion imaging, comprising:

an input interface for receiving a frequency for an oscillatory motion of an X-ray scanner's X-ray source around an object during a perfusion imaging session where a sequence of projection images are acquired of the object whilst contrast agent is at least partly perfusing at least a region of the object, the perfusion resulting in an X-ray attenuation signal (TAC) for that object region. The received frequency of the X-ray source's oscillatory motion defines a sampling rate for the X-ray attenuation signal (TAC). A sequence of image points across the acquired sequence of projection images represents a temporal sample of said X-ray attenuation signal (TAC) for the object region or the temporal sample of said X-ray attenuation signal (TAC) may be obtained by applying at least in parts a tomographic reconstruction method to the points of the sequence of projection images.

The apparatus further comprises a control unit configured to use the received sampling frequency to generate a control signal for an injector unit to deliver the contrast agent to the object at a variable discharge or injection rate. The control signal, when applied to the injector unit, causes the contrast agent injection rate to vary over time according to a periodic signal of pulses. The periodicity of the pulsed signal is computed by the controller as a function of the sampling rate or frequency so as to mitigate temporal signal aliasing in the X-ray attenuation signal sample.

Put differently, the contrast material is injected into a patient's vascular system by controlling a power injector ("pump") in a predefined repeated, periodic manner instead of a single bolus injection. The repeated contrast signal has a frequency-discrete spectrum and is distinguished from the continuous spectrum of a single bolus injection. The specification of the repeated injections, that is periodicity and pulse width, is adjusted to the speed of the C-arm system. The injection periodicity is selected to avoid or at least substantially mitigate or eliminate signal aliasing caused by the low rotation speed of the C-arm system. Aliasing would cause the TAC sample to include the aliasing frequencies as spurious components thereby rendering the subsequent reconstruction and estimation of the perfusion parameters less accurate. In other words the apparatus for supporting perfusion imaging makes use of a specific contrast injection protocol that allows extracting dynamic perfusion parameters such as Blood Flow and Mean Transit Time on a sufficient level of accuracy. The method takes into account the slow rotational speed of a C-arm based X-ray system which must be capable of repeated forward/backward short scan sweeps. As proposed herein the controller is configured to account for image acquisition gaps (i.e. delay times) at the C-arm's turning points.

The apparatus affords improved workflow for many X-ray guided interventional procedures. The apparatus allows substantially fully temporally resolved quantitative perfusion imaging without the need for fast rotational image acquisitions. In other words, dynamic perfusion parameters measuring the velocity of blood flow (such as CBF) can be obtained so there is no restriction to mere static perfusion parameters such as CBV where it is only the blood concentration that is captured.

According to one embodiment, the controller configured to mitigate the aliasing by adjusting the frequency of at least one of the pulsed injection rate signal's harmonics so that the adjusted frequency of the at least one harmonic differs by at least a user-definable/preset margin from each of the frequencies of the alias-components in the frequency spectrum of the X-ray attenuation signal sample.

According to one embodiment the controller is configured to adjust the ratio between the pulse width and the period so as to essentially suppress a selectable one of the pulsed injection rate signal's harmonic. According to one embodiment the ratio is 1/3 so as to suppress the third harmonic.

According to one embodiment the controller is configured to control the injector to deliver the contrast agent in a phase prior to commencement of the image acquisition session by the scanner. This avoids recording transient features that occur shortly after injection. The delay allows the contrast agent to settle before commencing with the image acquisition.

According to one embodiment the apparatus further comprises a signal processor configured to process the acquired sequence of projection images to extract at least one harmonic from the sampled TAC by fitting to the sample TAC at least one basis function of a family of basis functions, the basis function corresponding in frequency to the frequency of the at least one harmonic of the discharge rate signal. According to one embodiment a dedicated dynamic tomographic reconstruction method is used to estimate certain features (e.g. the harmonics of the injection periodicity) of the contrast TACs at a specified image region representative of the region of interest. Reconstruction of the fully detailed TACs is not required. A dynamic tomographic reconstruction method incorporates a temporal model that includes knowledge on the periodicity of the contrast agent injection signal. The dynamic tomographic reconstruction method can be said to be dedicated because it uses a model of (Fourier)-basis functions that includes the first N (N is user selectable) harmonics of the TAC. The reconstruction method as proposed herein is hence tailored to the spectral characteristics of the TAC because it has been recognized that the TAC harmonics essentially correspond to integer (1, 2, 3, . . . ) multiples of the selected bolus injection frequency.

According to one embodiment the family of basis functions includes a linearly rising function. This allows accounting for the long-term accumulation of contrast agent because this effect has been observed to result in step-wise increase of contrast levels as recorded by the TAC.

According to one embodiment the signal processor is configured to fit the at least one basis function to a TAC for an image region representative of a supply path through which the contrast agent is supplied to the object, the signal processor then convolving the supply path TAC with any one of at least two pre-selected model impulse response functions each representative of the material composition of the imaged object region, the signal processor then comparing any one of the so obtained convolved functions with the TAC of the object region, the perfusion parameter evaluator then using, for the calculation of the perfusion parameter, the one of the convolved functions fitting best, according to a predefined criterion, to the TAC of the object region.

Put differently, perfusion analysis (to obtain e.g. CBF, CBV, MTT) is done by a dedicated method by making use of the estimated contrast features in the tissue and in an arterial region. According to one embodiment an implicit deconvolution approach is used by fitting a plausible model of a tissue response functions to the estimated contrast features.

In conclusion, as proposed herein a repeated contrast injection with a predefined periodicity, opposed to a single bolus injection is used in CT-perfusion imaging. The injection periodicity is adjusted to the rotational speed of the C-arm system in order to avoid or at least mitigate temporal signal aliasing. A temporal-model-based dynamic tomographic reconstruction method is applied to extract the lower order harmonics of the vascular system's responses to the periodic contrast injection. Finally, perfusion analysis is based on an implicit deconvolution approach that takes into account the extracted contrast harmonics.

The described apparatus may be put to use with any interventional X-ray C-arm system that is capable of an alternating forward/backward short-scan rotational acquisition in connection with a programmable contrast pump. Perfusion imaging during interventions is of particular interest in the fields on treatment planning and outcome control. Typical Cathlab applications include but are not restricted to carotid artery stenting, acute stroke treatment, tumor visualization and embolization, treatment of peripheral vascular diseases and SIM.

In short, it is proposed herein a periodic contrast injections signal and the analysis of its harmonics for the purpose of computing perfusion parameters in interventional X-ray perfusion imaging.

DEFINITIONS

By "interventional" X-ray imaging system, such as a C-arm scanner, is meant any rotational imaging system with relatively slow rotation of X-ray source/detector assembly. The rotation is slow if during imaging acquisition session, medial personal can safely operate on the imaged subject in close physical proximity without running the risk of being accidently hit by rotating components in a manner that would cause injury or harm to the personal.

"Pulse" as used herein to describe the non-zero injection rate is to be construed broadly. In particular its width as compared to the period between two consecutive pulses ("periodicity") may be a third of that periodicity or may even have a larger width. Pulse should not be limited to a narrow width with respect to the periodicity.

"Image session" is the period during which a defined number of scan sweeps are performed by the X-ray imager/scanner to acquire the sequence of projection images which are then processed together as described herein to so obtain the desired perfusion parameters.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
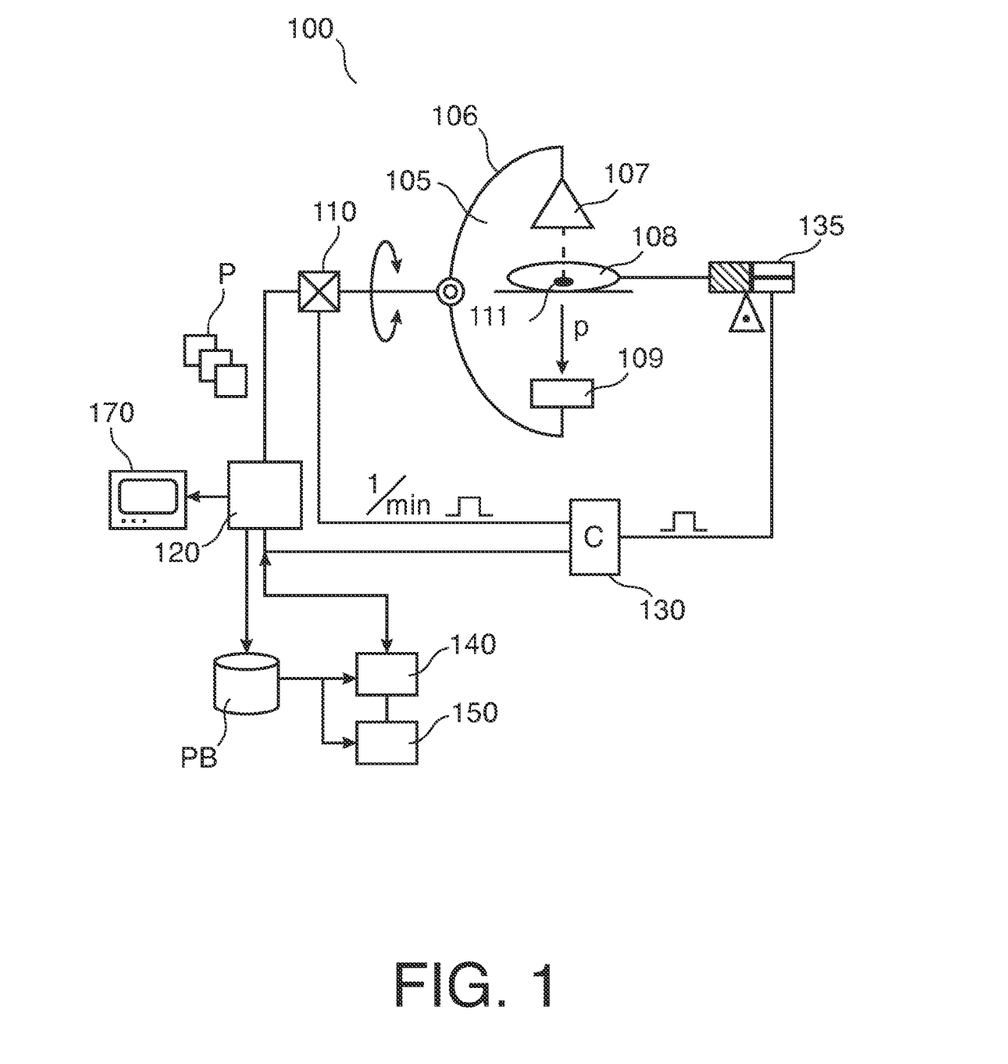
FIG. 1 shows an X-ray scanner arrangement for perfusion imaging including the perfusion image support apparatus.

With reference to FIG. 1, there is shown a perfusion imaging arrangement 100.

It includes an x-ray imager 105 of the C-arm type. X-ray imager 105 is used to acquire a sequence of x-ray projection images P of an organ of interest 111 to support an intervention.

In one embodiment, the organ of interest is a patient 108's heart or brain.

Patient 108 is placed on an examination table. Imager 105 comprises a rigid C-arm structure 106 journaled on a bearing. Journaling allows rotation of C-arm 140 around a at least one axis passing through journaling. C-arm structure 106 can thus be positioned at various rotation angles α around organ of interest 111.

C-arm 106 carries at one of its ends an x-ray source 107 and at the other end a detector 109 in opposed spatial relationship to said x-ray source 107. Detector 109 includes an array of detector cells (not shown).

During an imaging session, x-rays are emitted from x-ray source 107. X-rays pass through organ of interest 111 and are then detected at detector 109. The X-rays are formed from X-ray beams p.

Each x-ray beam p is attenuated as it passes through the object of interest 111 and impact on same. It is this attenuated x-ray beam that is detected at individual detector cells in detector 109.

The angle of incidence ("projection direction" or "view") at which the x-ray beam impacts region of interest 111 is defined by rotation or angulation angle α. In practice the C-arm may afford rotation around a plurality of axis, so the actual view is then defined by a tuple of angles (α, β, . . . ). The degree of attenuation experienced by each individual x-ray beam p depends on the type and amount of tissue the ray p is passing through. Each attenuated x-ray beam p impinges on a detector cell and generates there an electric signal anti-proportional to the degree of attenuation. The electric signal generated at each detector cell for an impinging x-ray beam p is then translated via a data acquisition module into a pixel value encoding a corresponding grey value in variance with the attenuation. The pixel values i,j form a matrix and are then stored as a sequence of projection images $P(\alpha, t_i)$ each taken at a particular projection direction α at time $t_i$.

The sequence P of projection images is acquired during the image acquisition session. Each individual projection image acquired for each single scan sweep $ds_i$ along different projection directions within an arc or action $\alpha_{min}$-$\alpha_{max}$ as indicted in FIG. 2. The sequence P of projection images may then be stored on a data base DB. The projection images P may be stored in the DICOM format. The DICOM format includes meta-data encoding for each projection image the projection direction at which it was acquired along with its acquisition time t.

Contrast agent is administered via a power injector 135 to patient's 108 blood prior to and during the image acquisition to have contrast agent perfuse the organ of interest or at least relevant parts thereof. Radiation opacity of contrast agent in tissue is higher than radiation opacity of soft tissue alone making up the region of interest 111. Over the passage of time during the imaging session, the volume ("bolus") of contrast agent administered in one injector 135 action cycle accumulates in the region of interest 111 and its concentration therein varies in time so grey values pixels making up the smeared out footprint of the bolus contrast likewise vary across the sequence of projection images P. Because of the contrast agent, in each projection image acquired in one scan sweep $ds_i$ of C-arm encodes a projection view or footprint of region of interest 111 along a different projection direction $\alpha_{min} \leq \alpha \leq \alpha_{max}$. The blood carrying contrast agent is flowing via a supply path SP, for example an artery, to the region of interest 111, thereby dispersing the contrast agent throughout said region of interest 111.

Overall operation of perfusion imaging system 100 is controlled by work station 120 having a console for receiving instructions by the medical professional.

Perfusion imaging system 100 further comprises a control unit 130 arranged to control operation of contrast agent injecting injector pump 135. There is also a signal processor 140 to process and track the contrast agent "footprints" as recorded in the sequence of projection images $P(\alpha, t_i)$ to so extract temporal spectral information from the sequence of images. The spectral information is then fed into perfusion parameter evaluator 150 where a number of relevant perfusion parameters are then computed and passed on to workstation 120. The perfusion parameters such as CBF (Cerebral blood flow), CBV (Cerebral blood volume), MTT (Mean transit time) describe clinically relevant aspects of perfusion. A set of perfusion parameters can be rendered for view in suitable diagrams on screen 170 so that the medical professional may deduce therefrom medically relevant clues in respect of the function of organ of interest 111. Operation of injector control unit 130, a signal processor 140 and perfusion parameter evaluator 150 will be described in more detail below, in particular with reference to FIGS. 4 and 5.

The components of FIG. 1, 130, 140, 150 are shown as separate modules arranged in a distributed architecture and connected in a suitable communication network. The components may be arranged as dedicated FPGAs or as hardwired standalone chips. However, this is an exemplary embodiment only. In alternate embodiments, the components of may be resident in work station 120 running as software routines. The components may be programmed in a suitable scientific computing platform such as Matlab® or Simulink® and then translated into C++ or C routines maintained in a library and linked when called on by work station 120.

Figure 2:
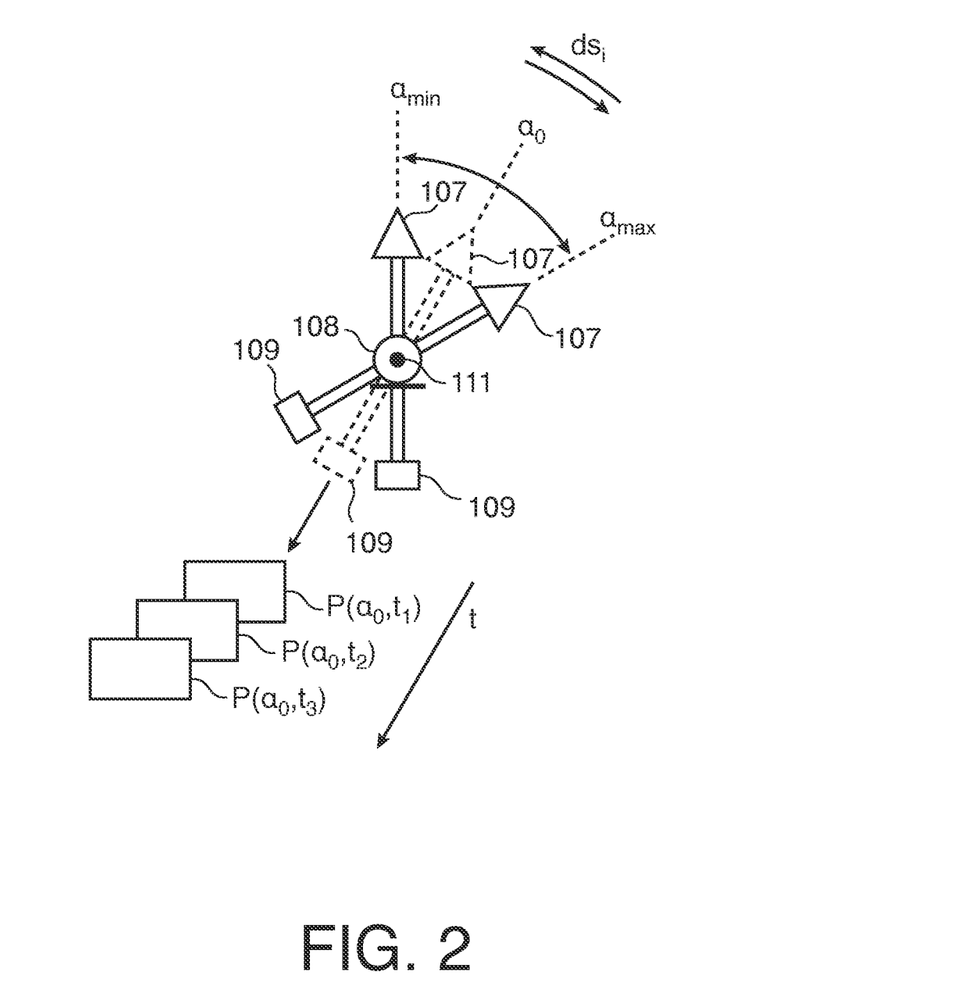
FIG. 2 shows operation of the arrangement of FIG. 1 during image acquisition.

Reference is now made to FIG. 2 showing a frontal elevation of scanner 105 during operation. The projection images $P(\alpha, t_i)$ acquired by C-arm 106 oscillating in backwards and for forward sweeps within the angulation range $\alpha_{min}$-$\alpha_{max}$.

Figure 5:
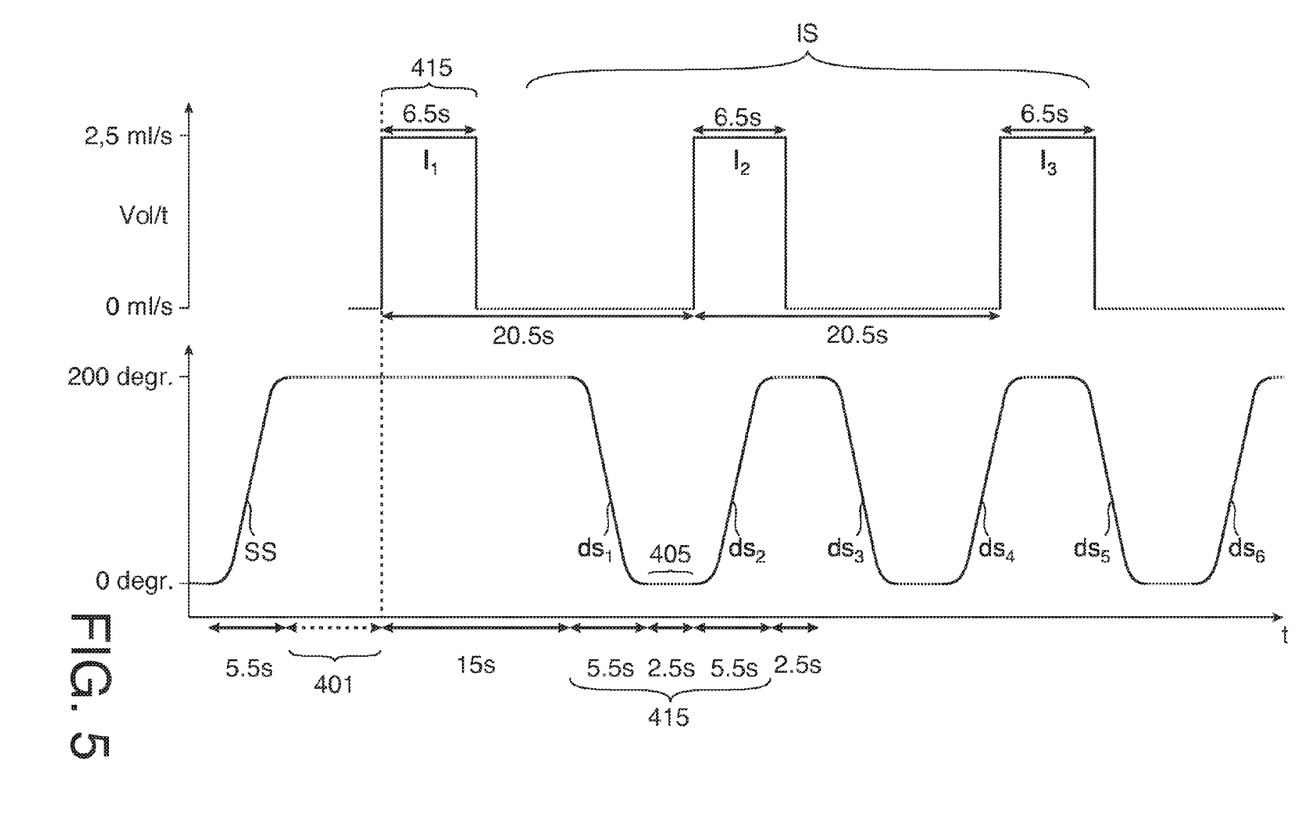
FIG. 5 is a timing diagram for an X-ray scanner and a contrast agent power injector.

The time-angulation diagram at the bottom of FIG. 5 shows as an example of a sequence of 6 image acquisition sweeps $ds_{1-6}$ alternating between forward and backward sweeps the work station 120 issuing respective toggle signals at the endpoints $\alpha_{min}$, $\alpha_{max}$ of the angular arch or swath swept out by C-arm 106. Time index $t_i$ for each projection image $P(\alpha, t_i)$ indicates the timing in each sweep $ds_i$ where the C-arm assumes view $\alpha_0$. It takes up to $t_i$-$t_{i+1}$ time for C-arm to repeatedly assume any given view $\alpha_0$ during either a forward or a backward sweep. This is the sampling period determining the sampling rate as afforded by scanner 105.

A static sweeps ss is executed in a preparatory phase prior to commencement of the sequence of dynamic sweeps $ds_i$. There is yet no contrast agent present in the organ of interest 111 during the single static sweep ss whereas contrast agent is present during the sequence of dynamic sweeps $ds_i$. The projection images acquired in the static sweep may then be used to background-correct the images acquired in the dynamic sweeps $ds_i$.

Acquired projection images $P(\alpha, t_i)$ may then be stored either on work station 120 or a database DB. Projection images P are made up of a matrix i,j of numerical pixel values. Each pixel value describes the attenuation of the contrast agent at the point of the organ represented by that pixel element.

Figure 3:
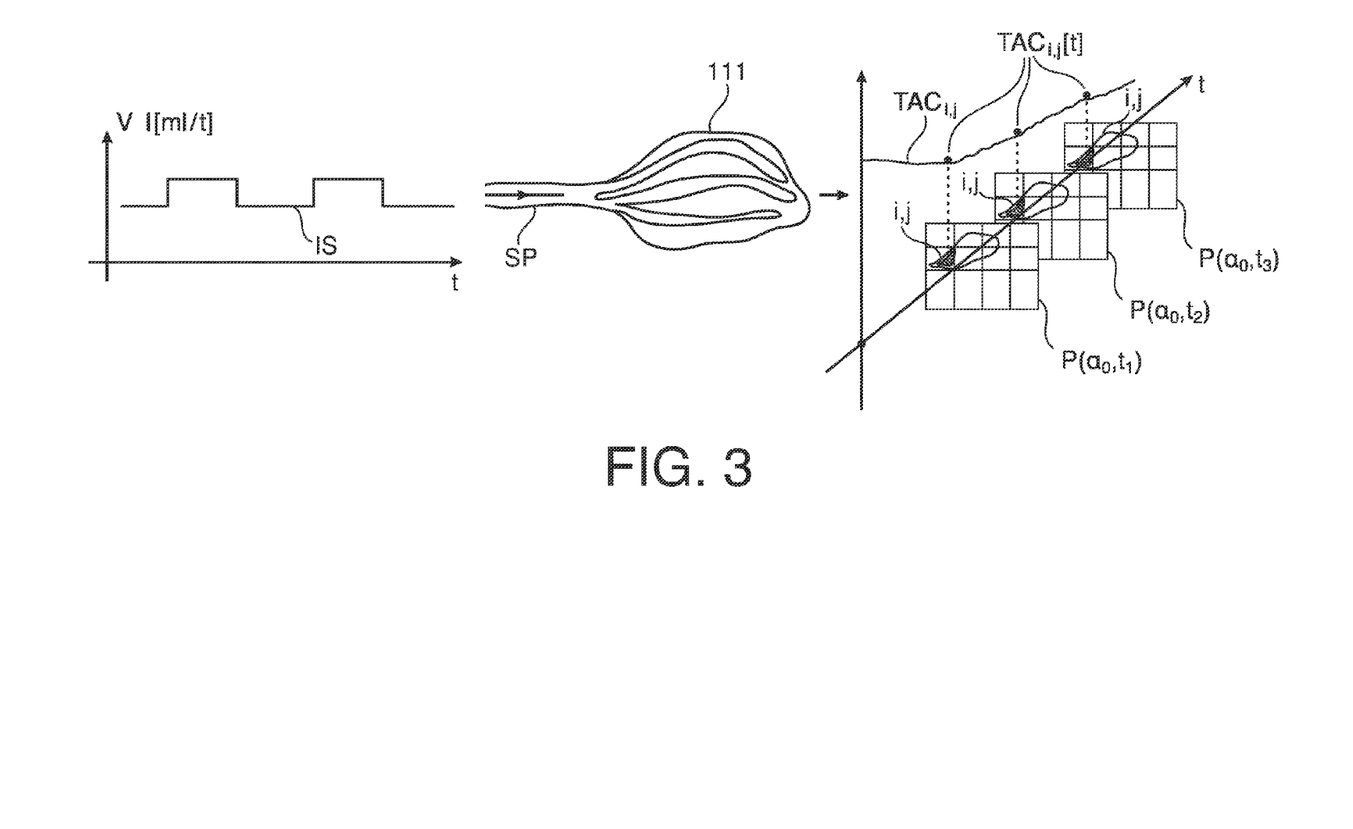
FIG. 3 is a schematic diagram showing the perfusion process and the various signals involved.

FIG. 3 is a schematic diagram of the perfusion process and the various signals involved. The injection rate signal IS ("bolus signal") as generated herein is a periodic signal with each of its "pulses" $I_i$ representing a single bolus so the total quantity of contrast agents is supplied in repeated boluses. The injection rate signal IS is a time series describing how the injection rate varies. The area under that curve is a measure for the total amount of contrast agent injected. The contrast agent is supplied to the region (organ of interest) via the relevant supply path SP, for example an artery feeding into the organ 111's local vasculature. The organ of interest interacts with bolus thereby "distorting" the bolus signal into a family of local time-attenuation curves $TAC_{i,j}$. So the TAC may be said to form an organ specific response signal to the bolus input signal IS.

According to one embodiment, the sample $TAC_{i,j}[t]$ of each local $TAC_{i,j}$ is provided by the set of corresponding image elements i,j (neighborhood of pixels) across the sequence of the acquired projection images $P(\alpha_0, t_i)$. The image elements i,j of different projection images "correspond" if they have been caused by a pencil X-ray beam that passed through essentially the same point of the organ of interest during acquisition of the respective images of the sequence of projection images $P(\alpha_0, t_i)$. In other words image elements having the same row and column across the sequence of images form the $TAC_{i,j}$ sample for the image element i,j representing a portion of the organ of interest. Signal processor 140 is configured to then translate by reconstruction the TAC sample from "projection space" is into a TAC sample in 3D space As explained in more detail below in relation to operation of signal processor 140, this TAC sample in "projection space" is then translated or transformed into sample $TAC_{i,j}[t]$ in 3D space. The 3D sample TAC is obtained from a collection of voxels that result as an intermediate result when a dynamic tomographic method is applied to the projection images $P(\alpha_0, t_i)$. The 3D sample TAC is obtained in the form of a sequence of voxels by first applying at least partly the dynamic tomographic method to the projection images $P(\alpha_0, t_i)$.

In contrast to fast rotating standard CT systems, the interventional X-ray imaging system is mounted on an open C-arm device that has limited rotational capabilities in terms of speed and movement range. Due to scanner 105's mechanical arrangement as an interventional system, C-arm 106 action is restricted to slow so called "short scan" movements during projection image acquisition session, its swath or action range $\alpha_{min}$-$\alpha_{max}$ being slightly more than a half circle rotation.

For a repeated coverage of this angular range over an extended time span, the C-arm 106 needs to turn round its rotational direction at the end of each scan sweep, and a toggled forward/backward sweep mode is performed. Furthermore, the C-arm 106's rotation speed is typically low, e.g. 5.5 seconds for a single short scan sweep. An additional delay 405 of 2.5 seconds (typical) is required when turning directions between forward and backward sweeps $ds_i$, $ds_{i+1}$, i.e. the C-arm has to take a rather long pause after each sweep.

Hence, 8 s<$t_i$-$t_{i+1}$<16 s so it typically takes between 8 and 16 seconds for C-arm 106 to repeatedly reach a certain angular viewing position $\alpha_0$. In terms of temporal sampling, such a low sampling rate (0.0625 Hz to 0.125 Hz) is not sufficient to capture the fast dynamics of the TACs that would result had only a single (and not a repeated one as described herein) bolus contrast injection been used. The continuous frequency spectrum of a typical TAC in an artery after a single bolus injection can contain significant signal components up to 0.1 Hz. See for example P. Montes, "Dynamic Cone-beam Reconstruction for Perfusion Computed Tomography", PhD thesis, Univ. Heidelberg, (2006). In this case, due to temporal signal aliasing, an exact recovery of TACs is not possible given the current C-arm's limitations described above.

For such typical arterial TAC the traditional Nyquist sampling theorem would state a minimum sampling rate of 0.2 Hz of the system for exact TAC reconstruction which corresponds to the requirement of 2.5 seconds maximum sweep time (including the delay) of the C-arm system. Such a fast rotating C-arm system is currently not feasible in interventional settings.

Overall Operation

In a first step, blood perfusion imaging is implemented by tracking over time (e.g. for 40 seconds) the spatial distribution of X-ray-opaque contrast agent that is administered to the patient's vascular system by way of injector 135 (as controlled by controller 130) in repeated boluses injected during the course of the imaging session. As indicated earlier in relation to FIG. 3, in one embodiment bolus tracking is realized by signal processor 140 implementing a dynamic tomographic reconstruction method. An intermediate result thereof is the contrast time attenuation curve TAC—or some features of same, e.g. its harmonics—for each voxel in the generated volumetric image.

In a second step, the TACs in soft tissue are normalized by means of deconvolution against an arterial input TAC in order to obtain a tissue impulse response function. The deconvolution step requires an accurate estimation of the contrast TACs in the regions of interest. In a final step, a set of perfusion parameters (e.g. Cerebral blood flow (CBF), Cerebral blood volume (CBV), Mean transit time (MTT)) is computed by analysis of the tissue impulse response functions according to linear systems' theory. Details of each of the three steps will be provided below.

Operation of Injector Controller 130

Broadly speaking, apparatus 130 operates to adjust the bolus injection signal to so mitigate temporal aliasing effects in the TAC signal sample.

The periodicity of repeated contrast injections is chosen according to the rotational speed of the C-arm system. The rotational speed determines the tomographic system's sampling rate. E.g. for a C-arm that performs toggled forward/backward short scan sweeps $ds_i$ of 5.5 seconds duration each and 2.5 seconds delay between the sweeps, it takes 16 s (=2*8 s) maximum to reach a certain angular position. This corresponds to 0.0625 Hz sampling rate. The contrast injection periodicity is selected by controller 130 to avoid or at least mitigate aliasing caused by the sampling. A chosen periodicity of e.g. 20.5 seconds for a rectangular bolus injection signal corresponds to a discrete signal spectrum with harmonics at f0=0 Hz, f1=0.0488 Hz, f2=0.0976 Hz, f3=0.1463 Hz, etc. An exemplary rectangular bolus injection rate signal IS is shown in the upper part of FIG. 5. The periodicity is measured between the rising edges of two consecutive bolus pulses $I_i$, $I_{i+1}$. The first bolus shot or pulse $I_1$ is administered after expiry of an arbitrary idle phase whilst C-arm resides in either one of turn around points $\alpha_{min}$, $\alpha_{max}$. First sweep $ds_1$ then commences after expiry of a settling phase to avoid recording of transient contrast agent features. In the example, the settling phase is 15 seconds into the bolus injection phase that is, the first sweep $ds_1$ commences after the rising edge of the first bolus pulse $I_1$.

Figure 4:
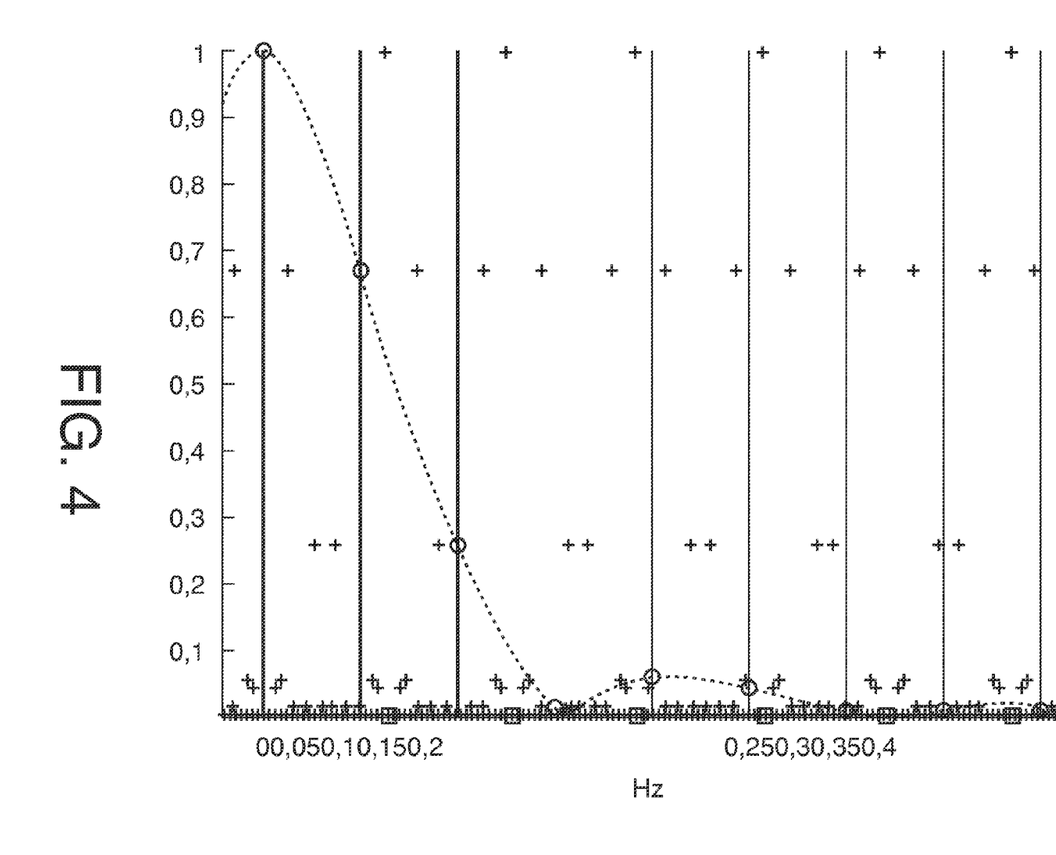
FIG. 4 is a frequency domain representation of signals processed and generated by the perfusion image support apparatus.

As shown in the aliasing diagram of FIG. 4, the risk of aliasing between the 0th, 1st, and (partially) 2nd harmonics is minimized, i.e., there is no overlap, safe for a certain amount of spectral leakage, between solid lines indicating the relevant frequencies f0, f1, f2 of the harmonics and the crosses indicating the frequencies of the aliasing components. The discrete spectrum of the bolus signal is indicted in FIG. 4 by circles. The aliasing components occur due to the sampling process and are obtained by shifting the bolus signal spectrum IS by integer multiples of the sampling C-arm frequency. As the vascular system is typically characterized as a low-pass system, higher frequency components (e.g. beyond 0.2 Hz) do practically not occur. The squares on frequency axis in FIG. 4 indicate the sampling rate of the rotation C-arm system.

Controller 130 receives via suitable interface means the C-arm sampling rate at which scanner 100 is to acquire projection images P. The sampling rate is defined by the time period it takes for the X-ray source to pass or revisit any given projection angle α0 within the angular action range $\alpha_{min}$-$\alpha_{max}$. After specifying the shape of the pules $I_i$ and based on the received C-arm sampling rate, controller 130 using Fourier analysis computes the first n harmonics of the bolus injection frequency. The computation is done by constructing the frequency domain representation as shown in FIG. 4 using an initial, tentative frequency for the bolus injection signal and the received C-arm sampling frequency. Using the specified pulse shape, the first n harmonics of said initial bolus injection signal are then calculated (see circles on solid vertical line in diagram of FIG. 4) and compared with the projections onto the frequency axis of the frequencies of the alias components. The alias components are indicated as a grid of crosses in FIG. 1 (negative frequency components are now show and because of symmetry need not be considered in the calculation).

The initial frequency is then incremented by controller 130 in suitably chosen increments, the frequency domain representation is re-computed and the harmonic frequencies are again compared with the alias component frequencies. This process is repeated in a computation loop until the frequencies of each of the first n harmonics is noted to deviate from each of the alias component frequencies by at least a pre-set margin $\Delta_{min}$. The so determined 0-th harmonic deviating by the desired margin from the alias component frequencies is then output as the adjusted bolus injection frequency and is then forwarded to the injector unit by suitable interface means. According to one embodiment the above incremental optimization is executed during image acquisition. In a preferred embodiment, the optimization is done in an up-front calibration step for a particular C-arm with fixed rotation speed and the so obtained bolus injection frequency is then likewise fixed and stored and then repeatedly used for controlling power injectors during perfusion imaging with the so calibrated C-arm scanner.

The dashed line in FIG. 4 shows the continuous spectrum of a single bolus injection as used in conventional systems which is in contrast to the repeated train of pulses forming the bolus injection signal of the present system having a discrete spectrum. The solid vertical lines show the harmonics of the train of pulses of the bolus injection signal shown in the upper part of FIG. 5 with bold vertical lines demarking the positions of the relevant harmonics positioned at least $\Delta_{min}$ apart from the alias component frequencies shown as crosses in FIG. 4. It has been found that using N+1 sweeps for N spectral components leads to satisfactory results. The larger the number of scan sweeps (preferably more than two) the larger the spatial resolution that can be achieved.

After the periodicity/frequency of the to be constructed injection signal IS is gotten by the above optimization, amplitude and pulse width is then specified. The bolus injection signal is then fully specified and suitable control parameters for frequency/periodicity, pulse width, pulse shape and amplitude can then be used to drive injector unit 135. Injector unit can then vary the injection rate in accord with the bolus injection signal so specified. Injection commences once trigger signal is issued by controller to the injector unit 130. An exemplary bolus injection rate signal IS having bolus pulses $I_i$ is shown in the upper part of FIG. 5.

According to one embodiment, the width of pulses $I_i$ for the injection signal IS can be chosen by a programmed modulation of the injection pump 140 to suppress undesired harmonics. For instance, the width of each bolus pulse $I_i$ may be set to approximately ⅓rd of the injection periodicity so the bolus pulse has a 6.5 s width which is about a third of a 20.5 s injection periodicity. In this case the 3rd harmonics (and multiples thereof) of the contrast signal IS are suppressed as can be seen in aliasing diagram of FIG. 4. Selecting and arranging for such a pulse/periodicity ratio further reduces the risk of signal aliasing caused by the slowly rotating C-arm.

In a preferred embodiment the shapes of the pulses are approximately rectangular as indicted in an idealized manner in the FIGS. 4, 5 enclosed herein. In this manner a periodic square or rectangular wave signal is effected. Other signal shapes however are also contemplated such as triangular wave form. Using a (substantially) triangular shape affords an even better suppression or damping of higher ranking spectral components (harmonics). In this case however the power injector must be capable of producing a triangular injecting rate profile.

In one embodiment, the repeated contrast injection should be started before the toggled C-arm acquisition is invoked. During that starting period a short-term transient phase of contrast injection should settle down; and the risk of acquiring transient signal components is reduced.

Operation of Signal Processor 140 for Perfusion Feature Extraction

Using the above computed bolus injection signal for controlling the injector, the series P of the projection images $P(\alpha, t_i)$ are acquired by imager 100 and then passed on as samples of the TAC in the relevant image portion representing the region of interest.

According to one embodiment, signal processor 100 is configured to merely extract a set of features of the TCA rather than reconstructing the entire TAC for the region of interest.

According to one embodiment it is only the first n (typically n<4, such as n=3) lower order signal harmonics that are extracted from the samples of the contrast TACs.

According to one embodiment a model-based dynamic tomographic reconstruction method is used such as the iterative dynamic reconstruction method described in Ch. Neukirchen, M. Giordano, S. Wiesner, "An iterative method for tomographic x-ray perfusion estimation in a decomposition model-based approach", Med. Phys. 37, 6125, (2010) or the analytic dynamic reconstruction method described in Ch. Neukirchen, "An Extended Temporal Interpolation Approach for Dynamic Object Reconstruction", Proc. Fully 3D reconstruction meeting, pp. 379-382, (2011).

When the dynamic tomographic reconstruction method is used, the TAC samples are obtained from a sequence of voxels that emerge during the reconstruction. Pixels from the sequence of Projection images $P(\alpha_0, t_i)$ are "collapsed" into a related voxel when evaluating line integrals during execution of the dynamic tomographic reconstruction method. The method can be halted once all the required Voxels forming the TAC[t] sample is gotten so save CPU time if a full reconstruction of the 3D slices is not required. Using this tomographic voxel based approach comes with the benefit of added accuracy so the sample better represents the underlying continuous TAC.

In one embodiment, signal processor 150, essentially a harmonic analyzer, is configured to use as a temporal model comprising a set of temporal basis functions that reflect some known characteristics of the bolus injection signal to effect a fitting to the TAC[t] sample. In one embodiment the 0th, 1st, and 2nd harmonics of the TAC is extracted, the set of temporal basis functions then includes the corresponding trigonometric Fourier functions of the bolus injection signal IS, i.e., a constant function, a sine and cosine at f1=0.0488 Hz, a sine and cosine at f2=0.0976 Hz for the 0th, 1st, and 2nd harmonics as shown in the example of FIG. 4.

According to one embodiment, a linearly rising temporal function is included in the set of basis functions. The linear function approximates and accounts for an effect of long-term contrast agent accumulation in the vascular system as experienced by the organ during injection. Typically this effect becomes apparent in the TACs as a step-wise increase of contrast levels. The final choice of such set of 6 temporal basis functions has the convenient property of being time invariant time-shift independent. The selection of an exact starting time for the toggled C-arm acquisitions with respect to the start of the injection is uncritical.

Using the pixel or voxel information from the relevant image portion in the across the sequence of projection images, parameters of the 6 basis functions are estimated. The parameters include "weights" (generalized Fourier coefficients). So in the example, there is a weight for the linear function and one for the 0-th harmonic and two weights for each (one for the real and one for the imaginary part of the weight expressed as a complex number) of the $1^{st}$ and $2^{nd}$ Harmonic. A total number of at least 6 C-arm sweeps is minimally required as shown in FIG. 5's timing diagram between the contrast injection protocol (upper part of FIG. 5) and the rotational acquisition protocol (lower part of FIG. 5). The parameters are the "coordinates" of the TAC in the function space spanned by the chosen temporal basis functions. The basis function coordinates are then used to reconstruct the frequency component of the first 3 harmonics of the TAC.

Operation of Perfusion Parameter Evaluator 150

The perfusion parameters (CBF, CBV, MTT, etc.) are computed by perfusion parameter evaluator 150 from the TACs' signal harmonics and the linearly rising function as extracted from the TAC and as previously reconstructed and estimated by signal processor 140.

Similar TAC harmonics are also extracted for all image elements ("tissue voxels") representative of the region of interest and for image elements representative of the supply path SP such as an artery. The artery TAC is the input function as mentioned earlier above in relation to FIG. 2 and the Models for the tissue impulse response functions are then computed either by implicit or by explicit deconvolution approaches for each tissue voxel TAC based on the theory linear systems. Only plausible tissue functional models are used taking into account physiological characteristics of the instant organ 111 so the shape of the resulting tissue impulse responses are constrained by those physiological characteristics. The number of effective model parameters for the tissue impulse response functions must be smaller or equal to the number of extracted TAC features. A maximum of 6 model parameters are afforded when using 6 temporal basis functions as in the example herein.

According to one embodiment perfusion parameter evaluator 150 implements an implicit deconvolution. An approximate TAC only based on the chosen temporal basis functions for the artery is computed from the harmonics extracted by signal processor 140. The approximate artery TAC is convolved by a set of plausible tissue impulse responses, resulting in a set of hypothetical tissue TACs. Approximate TACs are computed for all tissue voxels in the region of interest. Each approximate tissue TAC is compared with the TACs from the generated set of hypotheses and the closest (e.g. in a least squares sense) hypothetical TAC is determined. The tissue impulse response that is related to closest TAC is considered as the deconvolution and perfusion parameters can be derived from it.

The method as proposed herein does not merely teach the use of the injection of multiple contrast boluses but to adjust the bolus signal IS to have a fixed, predefined periodicity and to adjust same as a function of the rotational speed of the C-arm system. Because a fixed periodicity injection is used, the analysis into harmonics during dynamic reconstruction may be used so the number of parameters to be estimated can be reduced by restriction to the harmonics. X-ray dose to the patient can be likewise reduced because fewer sweeps are required. In the above example, the method as implemented above allows to for a mere 6 sweeps to compute the harmonics because the relevant perfusion parameters can be computed from these. Some parameters such as the CBV parameter can be calculated from the 0-th harmonic alone thus allows to reduce the number of sweeps even further down to two sweeps if CBV is the only parameter of interest.

Figure 6:
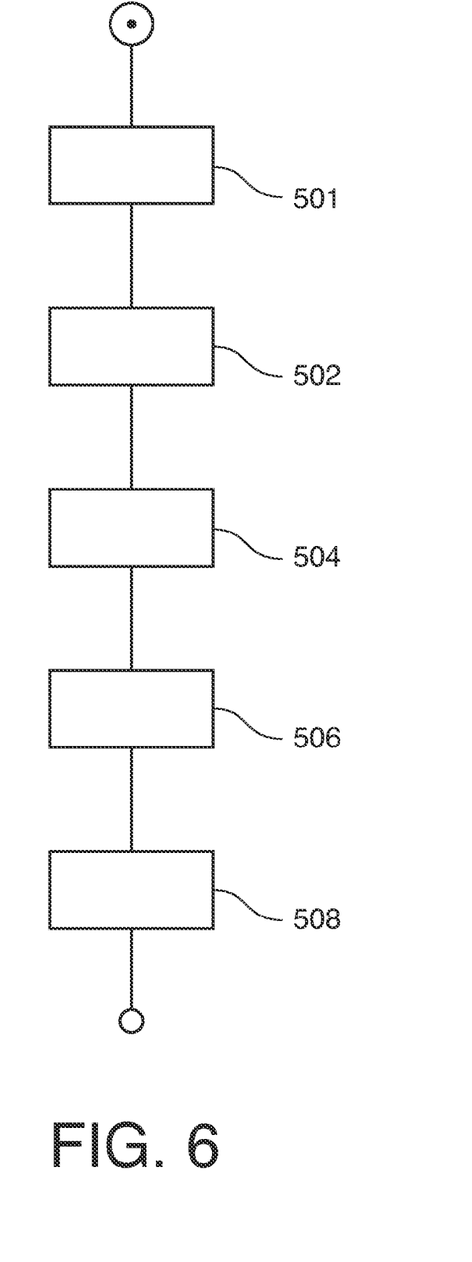
FIG. 6 is a flow chart of a method of supporting perfusion imaging.

With reference of flowchart of FIG. 6, the basic steps of a method of supporting perfusion imaging is summarized.

In step S501 the current C-arm sampling rate is received.

In step S502 a periodicity/frequency for a periodic pulsed bolus injection signal is determined as a function of the received sampling rate. The signal is determined so as to mitigate temporal signal aliasing in the X-ray attenuation signal sample.

The signal is for driving the power injector to administer the contrast agent to so have said agent perfuse the organ of interest during the imaging session.

Step S502 of determining the signal periodicity includes specifying the shape of the pulses.

In step S504, after having acquired the projection images in a perfusion imaging session using the determined pulsed bolus injection signal, harmonics of the sampled TAC signal are extracted by using basis functions for a tomographic reconstruction of the TAC signal that take account of the harmonics of the determined bolus injection signal.

In step S506 the extracted harmonics are used to compute perfusion parameters.

In step S508 the calculated perfusion parameters are output.

According to one embodiment the method is sample rate adaptive so the injection rate signal is re-calculated in response to receiving a new C-arm sampling rate.

According to one embodiment the IS specifying parameters of frequency, pulse width and shape is pre-calculated for a fixed C-arm sample rate and can then be used for future imaging sessions.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for supporting perfusion imaging, comprising:
    an input interface for receiving a frequency for an oscillatory motion of an X-ray scanner's X-ray source around an object during a perfusion imaging session where a sequence of projection images are acquired of the object whilst contrast agent is at least partly perfusing at least a region of the object, the perfusion resulting in an X-ray attenuation signal (TAC) for that object region, the received frequency of the X-ray source's oscillatory motion defining a sampling rate for the X-ray attenuation signal (TAC), image points across the acquired sequence of projection images representing a temporal sample of said X-ray attenuation signal (TAC) for the object region;
    a control unit configured to use the received sampling frequency to generate a control signal for an injector unit to deliver the contrast agent to the object at a discharge rate, the control signal, when applied to the injector unit, causing the contrast agent injection rate to vary over time according to a periodic signal of pulses, the period of the pulsed signal computed by the controller so as to mitigate temporal signal aliasing in the X-ray attenuation signal sample.

2. The apparatus of claim 1, the controller configured to mitigate the aliasing by adjusting the frequency of at least one of the pulsed injection rate signal's harmonics so that the adjusted frequency of the at least one harmonic differs by at least a user-definable/preset margin from each of the frequencies of the alias-components in the frequency spectrum of the X-ray attenuation signal sample.

3. The apparatus of claim 1, wherein the controller is configured to adjust the ratio between the pulse width and the period so as to essentially suppress a selectable one of the pulsed injection rate signal's harmonic.

4. The apparatus of claim 3, wherein the ratio is 1/3 so as to suppress the third harmonic.

5. The apparatus of claim 1, wherein the controller is configured to control the injector to deliver the contrast agent in a phase prior to commencement of the image acquisition session by the scanner.

6. The apparatus of claim 1, wherein the apparatus further comprises a signal processor configured to process the acquired sequence of projection images, preferably by tomographic reconstruction, to extract at least one harmonic from the sampled TAC by fitting in the reconstruction to the sample TAC at least one basis function of a family of basis functions, the basis function corresponding in frequency to the frequency of the at least one harmonic of the injection rate signal.

7. The apparatus of claim 6, wherein the family of basis functions includes a linearly rising function.

8. The apparatus of claim 6, wherein the apparatus further comprises a perfusion parameter evaluator configured to calculate based on the extracted frequency components at least one perfusion parameter including at least one of CBF, CBV, MTT.

9. The apparatus of claim 6, wherein the signal processor is configured to fit the at least one basis function to a TAC for an image region representative of a supply path through which the contrast agent is supplied to the object, the signal processor then convolving the supply path TAC with any one of at least two pre-selected model impulse response functions each representative of the material composition of the imaged object region, the signal processor then comparing any one of the so obtained convolved functions with the TAC of the object region, the perfusion parameter evaluator then using, for the calculation of the perfusion parameter, the one of the convolved functions fitting best, according to a predefined criterion, to the TAC of the object region.

10. An imaging system, comprising:
    an apparatus according to claim 1;
    the X-ray scanner;
    the injector unit.

11. The injector when controlled by the apparatus of claim 1.

12. A computer program element executable by a processor of the apparatus for supporting perfusion imagine, for the computer program element controlling the apparatus according to claim 1.

13. A non-transitory computer readable medium having stored thereon the program element of claim 12.

14. A method of supporting perfusion imaging, the method comprising:
  receiving a frequency for an oscillatory motion of an X-ray scanner's X-ray source around an object during a perfusion imaging session where a sequence of projection images are acquired of the object whilst contrast agent is at least partly perfusing at least a region of the object, the perfusion resulting in an X-ray attenuation signal (TAC) for that object region, the received frequency of the X-ray source's oscillatory motion defining a sampling rate for the X-ray attenuation signal (TAC), image points across the acquired sequence of projection images representing a temporal sample of said X-ray attenuation signal (TAC) for the object region;
  determining as function of the received sampling rate a periodic signal of pulses, the period of the pulsed signal computed by the controller so as to mitigate temporal signal aliasing in the X-ray attenuation signal sample, the periodic signal of pulses representing the variance over time of a contrast agent injection rate at which an injector unit delivers the contrast agent to the object.

15. The method of claim 14 further comprising:
  processing the acquired sequence of projection images preferably by tomographic reconstruction,
  extracting at least one harmonic from the sampled TAC by fitting to the sample TAC at least one basis function of a family of basis functions, the at least one basis function corresponding in frequency to the frequency of the at least one harmonic of the injection rate signal;
  computing based on the extracted frequency components at least one perfusion parameter including at least one of CBF, CBV, MTT.

16. A non-transitory computer readable medium comprising instructions, executable by a processor of an apparatus for supporting perfusion imaging, to cause the apparatus for supporting perfusion imaging to perform the method of claim 14.

17. A non-transitory computer readable medium comprising instructions, executable by a processor of an apparatus for supporting perfusion imaging, to cause the apparatus for supporting perfusion imaging to perform the method of claim 14.

* * * * *